(12) United States Patent
Dunn et al.

(10) Patent No.: US 8,648,993 B2
(45) Date of Patent: *Feb. 11, 2014

(54) COMBINED SERIAL/PARALLEL LIGHT CONFIGURATION AND SINGLE LAYER PCB CONTAINING THE SAME

(71) Applicant: Manufacturing Resources International, Inc., Alpharetta, GA (US)

(72) Inventors: William Dunn, Alpharetta, GA (US); David Williams, Canton, GA (US)

(73) Assignee: Manufacturing Resources International, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/678,226

(22) Filed: Nov. 15, 2012

(65) Prior Publication Data

US 2013/0278867 A1    Oct. 24, 2013

Related U.S. Application Data

(63) Continuation of application No. 12/693,148, filed on Jan. 25, 2010, now Pat. No. 8,351,013, which is a
(Continued)

(51) Int. Cl.
G02F 1/1333 (2006.01)
H05B 37/02 (2006.01)
A61N 5/06 (2006.01)

(52) U.S. Cl.
CPC .. *H05B 37/02* (2013.01); *A61N 5/06* (2013.01)
USPC ............................................ 349/161; 349/69

(58) Field of Classification Search
CPC .................................. H05B 37/02; A61N 5/06
USPC ...................................................... 349/69, 161
See application file for complete search history.

(56) References Cited

U.S. PATENT DOCUMENTS 4,093,355 A    6/1978  Kaplit et al.
4,593,978 A    6/1986  Mourey et al.
(Continued)

FOREIGN PATENT DOCUMENTS

GB     2402205     1/2004
JP     03153212    7/1991
(Continued)

OTHER PUBLICATIONS

Zeef, Hubing, EMC analysis of 18' LCD Monitor, Aug. 2000, 1 page.

*Primary Examiner* — Lucy Chien
(74) *Attorney, Agent, or Firm* — Standley Law Group LLP

(57) ABSTRACT

An LED circuit using a combination of series and parallel arrangements for optimum current sharing between LEDs. The current paths allow an LED to fail while minimizing the effect on other LEDs and noticeable luminance variance across the circuit. Some embodiments use metallic PCB technology which permits optimal thermal regulation of heat generated by the LEDs. Exemplary embodiments can be used with a single-layer PCB where only one layer of conducting material must be placed on the substrate. A constricted convection plate may be positioned behind the rear surface of the PCB to define a channel. One or more fans may be positioned to force cooling air through the channel. An LCD assembly using the same is also disclosed.

19 Claims, 6 Drawing Sheets

Related U.S. Application Data

(63) continuation-in-part of application No. 12/556,029, filed on Sep. 9, 2009, now Pat. No. 8,373,841, and a continuation-in-part of application No. 12/556,209, filed on Sep. 9, 2009, now Pat. No. 8,379,182, and a continuation-in-part of application No. 12/266,749, filed on Nov. 7, 2008, now Pat. No. 8,016,452, and a continuation-in-part of application No. 12/411,925, filed on Mar. 26, 2009, and a continuation-in-part of application No. 12/620,330, filed on Nov. 17, 2009, now Pat. No. 8,274,622, and a continuation-in-part of application No. 12/641,468, filed on Dec. 18, 2009, and a continuation-in-part of application No. 12/234,307, filed on Sep. 19, 2008, and a continuation-in-part of application No. 12/209,841, filed on Sep. 12, 2008, and a continuation-in-part of application No. 12/235,232, filed on Sep. 22, 2008, now abandoned.

(60) Provisional application No. 61/147,063, filed on Jan. 23, 2009, provisional application No. 61/153,148, filed on Feb. 17, 2009, provisional application No. 61/152,879, filed on Feb. 16, 2009, provisional application No. 61/252,295, filed on Oct. 16, 2009, provisional application No. 61/095,615, filed on Sep. 9, 2008, provisional application No. 61/095,616, filed on Sep. 9, 2008, provisional application No. 61/060,575, filed on Jun. 11, 2008, provisional application No. 61/039,454, filed on Mar. 26, 2008, provisional application No. 61/115,333, filed on Nov. 17, 2008, provisional application No. 61/138,736, filed on Dec. 18, 2008, provisional application No. 61/033,064, filed on Mar. 3, 2008, provisional application No. 61/060,504, filed on Jun. 11, 2008, provisional application No. 61/061,032, filed on Jun. 12, 2008.

(56) References Cited

U.S. PATENT DOCUMENTS

| | | |
|---|---|---|
| 4,634,225 A | 1/1987 | Haim et al. |
| 5,029,982 A | 7/1991 | Nash |
| 5,088,806 A | 2/1992 | McCartney et al. |
| 5,247,374 A | 9/1993 | Tereda |
| 5,559,614 A | 9/1996 | Urbish et al. |
| 5,598,068 A | 1/1997 | Shirai |
| 5,661,374 A | 8/1997 | Cassidy et al. |
| 5,748,269 A | 5/1998 | Harris et al. |
| 5,767,489 A | 6/1998 | Ferrier |
| 5,818,010 A | 10/1998 | McCann |
| 5,864,465 A * | 1/1999 | Liu ............................. 361/697 |
| 5,869,818 A | 2/1999 | Kim |
| 5,991,153 A | 11/1999 | Heady |
| 6,089,751 A | 7/2000 | Conover et al. |
| 6,157,432 A | 12/2000 | Helbing |
| 6,191,839 B1 | 2/2001 | Briley |
| 6,417,900 B1 | 7/2002 | Shin et al. |
| 6,535,266 B1 | 3/2003 | Nemeth et al. |
| 6,628,355 B1 | 9/2003 | Takahara |
| 6,642,666 B1 | 11/2003 | St-Germain |
| 6,839,104 B2 | 1/2005 | Taniguchi et al. |
| 6,885,412 B2 | 4/2005 | Ohnishi et al. |
| 6,943,768 B2 | 9/2005 | Cavanaugh et al. |
| 6,949,772 B2 | 9/2005 | Shimizu |
| 7,045,828 B2 | 5/2006 | Shimizu |
| 7,250,637 B2 | 7/2007 | Shimizu |
| 7,259,403 B2 | 8/2007 | Shimizu |
| 7,284,874 B2 | 10/2007 | Jeong |
| 7,375,381 B2 | 5/2008 | Shimizu |
| 2002/0101553 A1 | 8/2002 | Enomoto et al. |
| 2002/0126248 A1 | 9/2002 | Yoshida |
| 2003/0007109 A1 | 1/2003 | Park |
| 2004/0036834 A1 | 2/2004 | Ohnishi et al. |
| 2004/0165139 A1 | 8/2004 | Anderson et al. |
| 2006/0082271 A1 | 4/2006 | Lee et al. |
| 2006/0092348 A1 | 5/2006 | Park |
| 2006/0125418 A1 | 6/2006 | Bourgault |
| 2006/0132699 A1 | 6/2006 | Cho et al. |
| 2006/0177587 A1 | 8/2006 | Ishizuka |
| 2006/0209266 A1 | 9/2006 | Utsunomiya |
| 2007/0151664 A1 | 7/2007 | Shin |
| 2009/0009102 A1 | 1/2009 | Kahlman et al. |
| 2010/0307800 A1 | 12/2010 | Wee |

FOREIGN PATENT DOCUMENTS

| | | |
|---|---|---|
| JP | 08194437 | 7/1996 |
| JP | 11160727 | 6/1999 |
| JP | 2002158475 | 5/2002 |
| JP | 2005134849 | 5/2005 |
| JP | 2006145890 | 6/2006 |
| JP | 200803481 | 2/2008 |
| KR | 1020070070675 | 7/2007 |
| KR | 1020080000144 | 1/2008 |
| KR | 1020080013592 | 2/2008 |
| KR | 1020080086245 | 9/2008 |
| WO | 2005051054 | 6/2005 |
| WO | WO2005079129 | 8/2005 |

* cited by examiner

COMBINED SERIAL/PARALLEL LIGHT CONFIGURATION AND SINGLE LAYER PCB CONTAINING THE SAME

CROSS-REFERENCE TO RELATED APPLICATIONS

This application is a continuation of U.S. application Ser. No. 12/693,148 filed on Jan. 25, 2010. U.S. application Ser. No. 12/693,148 is a non-provisional application of U.S. Application No. 61/147,063 filed Jan. 23, 2009. U.S. application Ser. No. 12/693,148 is also a non-provisional application of U.S. Application No. 61/153,148 filed Feb. 17, 2009. U.S. application Ser. No. 12/693,148 is also a non-provisional application of U.S. Provisional Application No. 61/152,879 filed Feb. 16, 2009. U.S. application Ser. No. 12/693,148 is also a non-provisional application of U.S. Provisional Application No. 61/252,295 filed Oct. 16, 2009. U.S. application Ser. No. 12/693,148 is also a continuation-in-part of U.S. application Ser. No. 12/556,029 filed Sep. 9, 2009, which is a non-provisional application of U.S. Provisional Application No. 61/095,615 filed Sep. 9, 2008. U.S. application Ser. No. 12/693,148 is also a continuation-in-part of U.S. application Ser. No. 12/556,209 filed Sep. 9, 2009, which is a non-provisional of U.S. Provisional Application No. 61/095,616 filed Sep. 9, 2008. U.S. application Ser. No. 12/693,148 is also a continuation-in-part of U.S. application Ser. No. 12/266,749 filed Nov. 7, 2008, which is a non-provisional application of U.S. Provisional Application No. 61/060,575 filed Jun. 11, 2008. U.S. application Ser. No. 12/693,148 is also a continuation-in-part of U.S. application Ser. No. 12/411,925 filed Mar. 26, 2009, which is a non-provisional application of U.S. Provisional Application No. 61/039,454 filed Mar. 26, 2008. U.S. application Ser. No. 12/693,148 is also a continuation-in-part of U.S. application Ser. No. 12/620,330 filed Nov. 17, 2009, which is a non-provisional application of U.S. Provisional Application No. 61/115,333 filed Nov. 17, 2008. U.S. application Ser. No. 12/693,148 is also a continuation-in-part of U.S. application Ser. No. 12/641,468 filed Dec. 18, 2009, which is a non-provisional application of U.S. Provisional Application No. 61/138,736 filed Dec. 18, 2008. U.S. application Ser. No. 12/693,148 is also a continuation-in-part of U.S. application Ser. No. 12/234,307 filed Sep. 19, 2008, which is a non-provisional application of U.S. Provisional Application No. 61/033,064 filed Mar. 3, 2008. U.S. application Ser. No. 12/693,148 is also a continuation-in-part of U.S. application Ser. No. 12/209,841 filed Sep. 12, 2008, which is a non-provisional application of U.S. Provisional Application No. 61/060,504 filed Jun. 11, 2008. U.S. application Ser. No. 12/693,148 is also a continuation-in-part of U.S. application Ser. No. 12/235,232 filed Sep. 22, 2008, which is a non-provisional application of U.S. Provisional Application No. 61/061,032 filed Jun. 12, 2008. All aforementioned applications are hereby incorporated by reference in their entirety as if fully cited herein.

TECHNICAL FIELD

Exemplary embodiments relate generally to a circuit configuration for illumination devices and more specifically to a series and parallel configuration of LED lights on a single-layer PCB board.

BACKGROUND OF THE ART

In various lighting applications, a plurality of concerns have prompted the lighting industry to begin utilizing light emitting diodes (LEDs) and other new lighting technologies for providing the illumination source. Often, LEDs and these other illumination devices may be connected in series. However, when a single light fails, current will no longer pass through the lights and their illumination will cease. Also typically multiple-layer PCB boards must be used.

SUMMARY OF THE EXEMPLARY EMBODIMENTS OF THE INVENTION

Exemplary embodiments may connect LEDs in both series and parallel. This connection allows current to flow around an LED that has failed, so that the remaining lights in the assembly may continue to provide illumination.

Exemplary embodiments may also mount the LEDs on a printed circuit board (PCB) which has low thermal resistivity between the surface containing the LEDs and the opposite surface. The opposite surface may be metallic, and air may be forced over this surface in order to cool the assembly. A metallic core PCB board may be used. In exemplary embodiments, a single layer PCB board may be used. A constricted convection plate may be positioned behind the PCB to define a cooling channel. A fan may then be positioned to force cooling air through the channel, in order to cool the PCB/LED assembly.

BRIEF DESCRIPTION OF THE DRAWINGS

A better understanding of the exemplary embodiments will be had when reference is made to the accompanying drawings, wherein identical parts are identified with identical reference numerals, and wherein.

DETAILED DESCRIPTION OF A PREFERRED EMBODIMENT

Figure 1:
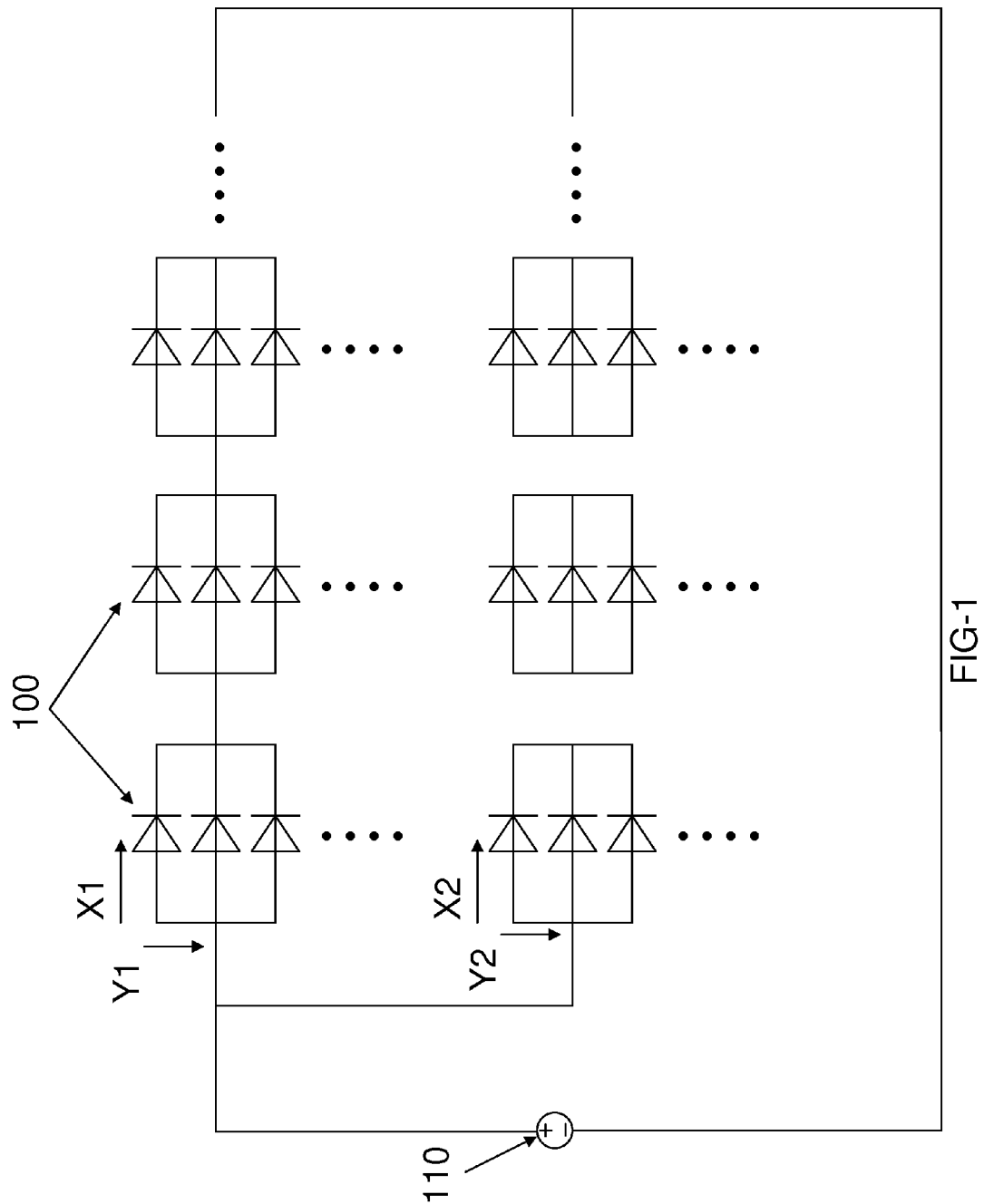
FIG. 1 is a schematic circuit diagram of various embodiments.

Turning to the drawings for a better understanding, FIG. 1 shows a plurality of lights 100 which are electrically connected to a power source 110 in both series and parallel. Several groups of lights 100 are shown. The groupings can be described in reference to the X1, X2, Y1, and Y2 dimensions shown. First, in the X1-Y1 dimension, three lights are shown in parallel groups with each parallel group being in series with one another. The 'dots' on the figure indicate that more than three lights may be in each parallel group. Thus, in the Y1 direction for each parallel group there may be more than three lights. Also, 'dots' are again used to represent that there may be more than three parallel groups. Thus, in the X1 direction there may be more than three parallel groups in series with one another.

Second, in the X2-Y2 dimension, three lights are shown in parallel groups with each parallel group being in series with one another. The 'dots' on the figure again indicate that more than three lights may be in each parallel group. Thus, in the Y2 direction for each parallel group there may be more than three lights and in the X2 direction there may be more than three parallel groups in series with one another. It should be noted that although four dots are shown that does not limit the embodiments to only four additional lights as any number of additional lights may be used.

Figure 2:
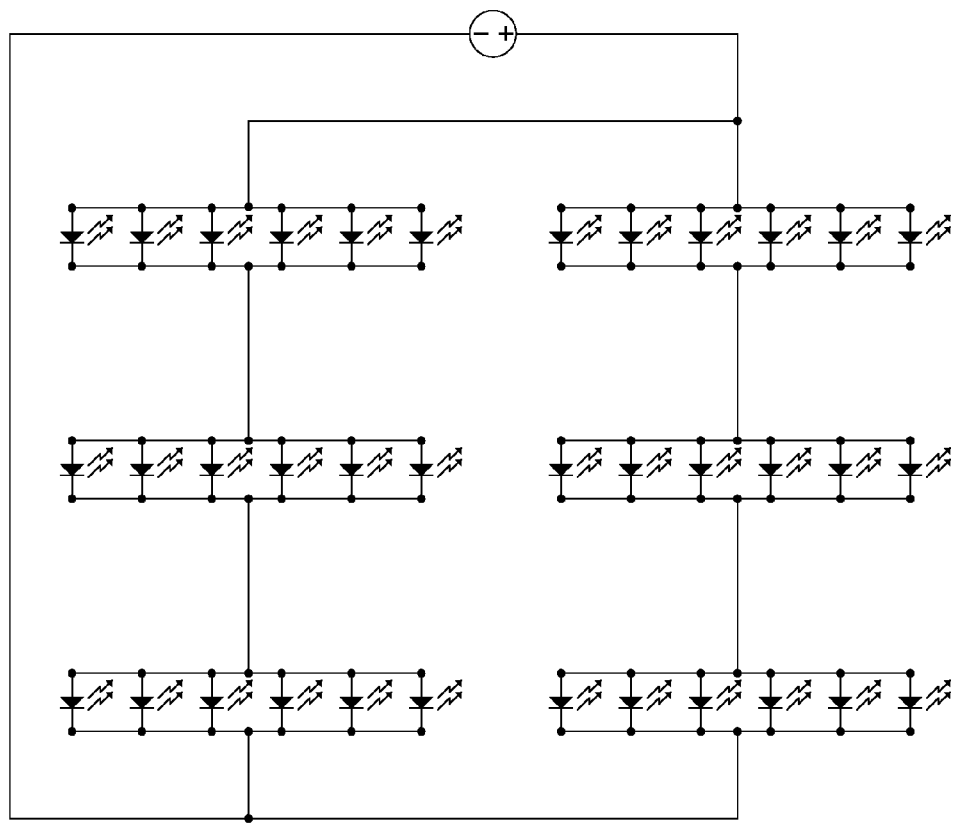
FIG. 2 is a schematic circuit diagram of an exemplary embodiment.

FIG. 2 shows an exemplary embodiment where each parallel group contains six lights and three parallel groups are in series with one another. This setup is doubled, and the two are then in parallel with one another. This embodiment may provide exemplary current sharing amongst the lights. Further, a single layer board may be used which is cheaper and easier for manufacturing purposes. The precise number and orientation of the lights may depend upon the properties (ex. current draw) of each light and the amount of illumination that is desired.

Should any of the lights fail, current may pass through any of the other lights within the parallel group, and subsequently through the remaining groups in the series connection. The groupings distribute the current so that the light which has gone out becomes more difficult to observe due to the uniformity of current sharing.

Referring back to FIG. 1, it should be noted that further parallel groups could also be added, ex. X3-Y3, X4-Y4, etc. Furthermore, the circuitry may contain additional elements such as amplifiers, limiters, microprocessors, resistors, capacitors, and measurement devices to further improve the performance of the circuit.

The lights and the circuitry may be a portion of a printed circuit board (PCB). The PCB may comprise a standard FR4 circuit board. An exemplary embodiment may utilize a low level of thermal resistance between the lights and the rear surface of the PCB. This allows heat to dissipate from the lights to the rear of the PCB where it may be removed from the lighting assembly by convection or conduction or both. An exemplary embodiment may use a metal core PCB for this purpose. The PCB for an exemplary embodiment may contain a metallic rear PCB surface where cooler air may pass over the surface and remove heat from the lighting assembly. In some embodiments the rear surface may also contain heat sinks or fins to facilitate the removal of heat from the PCB. The surface of the PCB which contains the lights may be coated with a highly reflective coating and may also be of a specific color, depending on the specific requirements for the lighting application.

Figure 3:
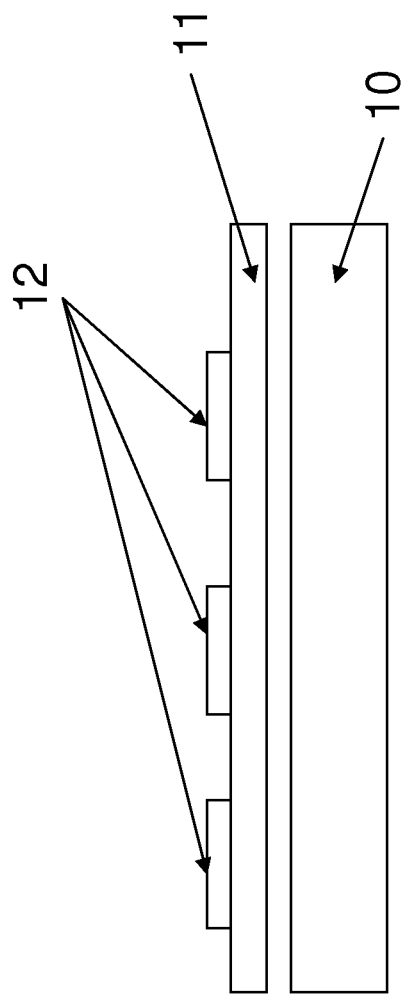
FIG. 3 is a side view showing the PCB layers.

FIG. 3 shows the layers for an exemplary PCB board. The substrate 10 preferably has a low thermal resistance. In a preferred embodiment the substrate 10 would be metallic and in an exemplary embodiment the substrate 10 would be aluminum. A dielectric material 11 may be placed between the conducting layer 12 and the substrate 10. The conducting layer 12 may be 1-2 oz copper. The dielectric material 11 may be 70-90 microns thick. This embodiment of the PCB is advantageous for several reasons. A single conduction layer can be used to connect all of the lights; this provides a reduced cost, weight, size, and thermal resistivity for the overall assembly. The metallic substrate also provides a low thermal resistivity and allows heat to more easily transfer between the front side of the PCB and the rear. The heat may be removed from the rear side of the PCB by moving air across the rear surface (with or without the optional thermally-conductive fins and/or heat sinks). The heat can also be removed from the PCB using any one of the techniques taught in co-pending applications: U.S. application Ser. No. 12/411,925 filed Mar. 26, 2009 which is a non-provisional application of U.S. Provisional Application No. 61/039,454 filed Mar. 26, 2008; U.S. application Ser. No. 12/620,330 filed Nov. 17, 2009 which is a non-provisional application of U.S. Provisional Application No. 61/115,333 filed Nov. 17, 2008; U.S. application Ser. No. 12/234,307 filed Sep. 19, 2008 which is a non-provisional application of U.S. Provisional Application No. 61/033,064 filed Mar. 3, 2008; U.S. application Ser. No. 12/209,841 filed Sep. 12, 2008 which is a non-provisional application of U.S. Provisional Application No. 61/060,504 filed Jun. 11, 2008; U.S. application Ser. No. 12/641,468 filed Dec. 18, 2009 which is a non-provisional application of U.S. Provisional Application No. 61/138,736 filed Dec. 18, 2008; U.S. Provisional Application No. 61/152,879 filed Feb. 16, 2009; U.S. application Ser. No. 12/556,029 filed Sep. 9, 2009 which is a non-provisional of U.S. Provisional Application No. 61/095,615 filed Sep. 9, 2008; U.S. application Ser. No. 12/556,209 filed Sep. 9, 2009 which is a non-provisional of U.S. Provisional Application No. 61/095,616 filed Sep. 9, 2008; and U.S. Provisional Application No. 61/252,295 filed Oct. 16, 2009 each of which are herein incorporated by reference in their entirety. The light circuit and associated PCB disclosed herein can also be uses in the advertising displays disclosed in co-pending U.S. application Ser. No. 12/266,749 filed Nov. 7, 2008 which is a non-provisional application of U.S. Provisional Application No. 61/060,575 filed Jun. 11, 2008, which is herein incorporated by reference in its entirety.

Figure 4:
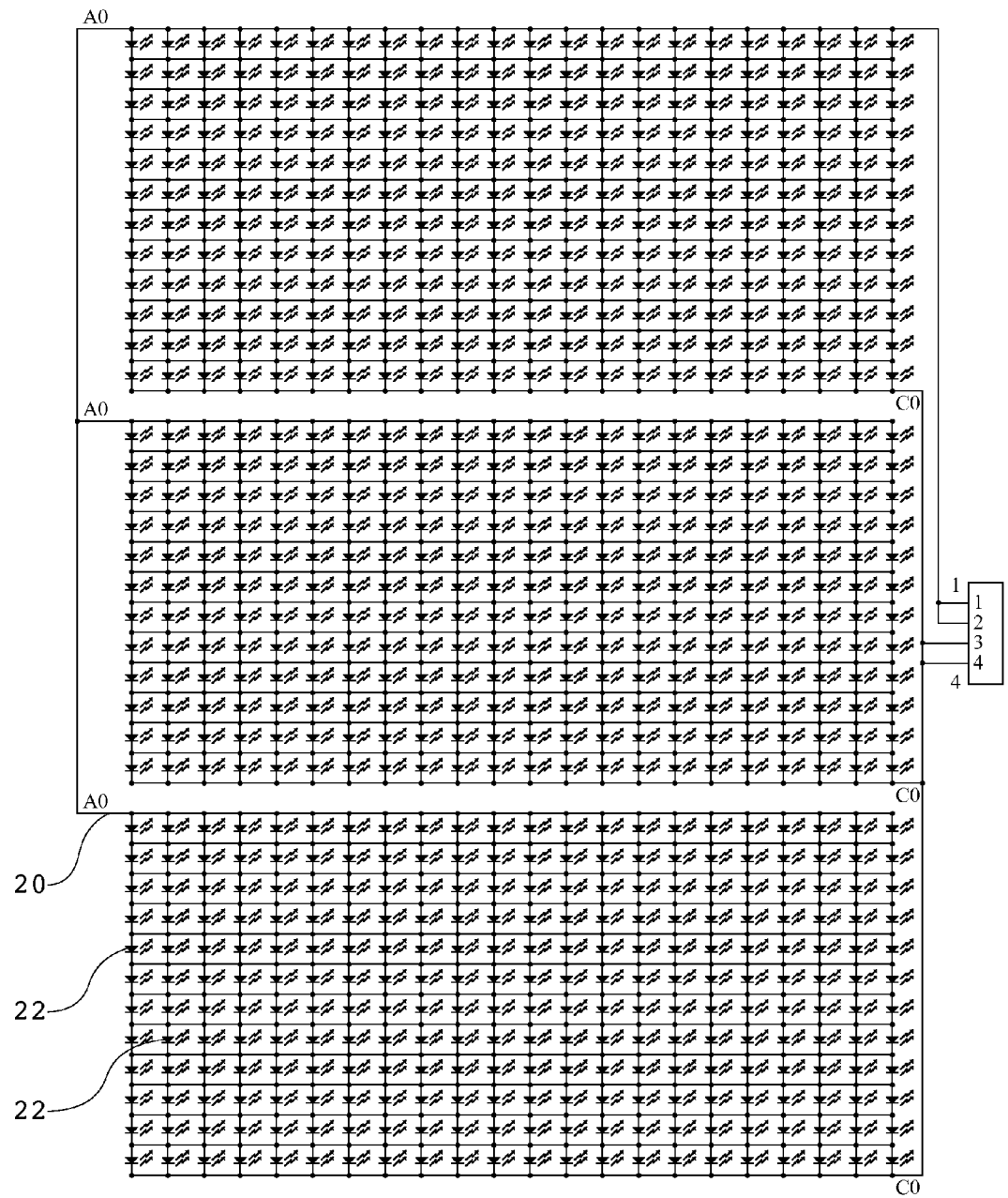
FIG. 4 is a schematic view showing one possible layout for a single layer PCB containing one embodiment of the serial parallel light circuit.

FIG. 4 shows one method for using a single layer of conduction lines to connect the lights on the PCB board. Obviously, the conduction lines 20 can be oriented in any number of designs and shapes for containing the circuit of lights 22. The precise routing of the conduction lines 20 may depend upon the number and size of light arrays that are being used and other components which are mounted on the PCB board. As shown in FIG. 4, the lights (sometimes LEDs) are arranged into three groups where each group has lights which are wired in both series and parallel.

Embodiments can be utilized for any variety of illumination applications, including but not limited to: backlighting for electronic displays, architectural lighting, advertisement lighting, effect lighting, or backlighting for static displays. Embodiments may use any type of light-emitting diode.

Figure 5A:
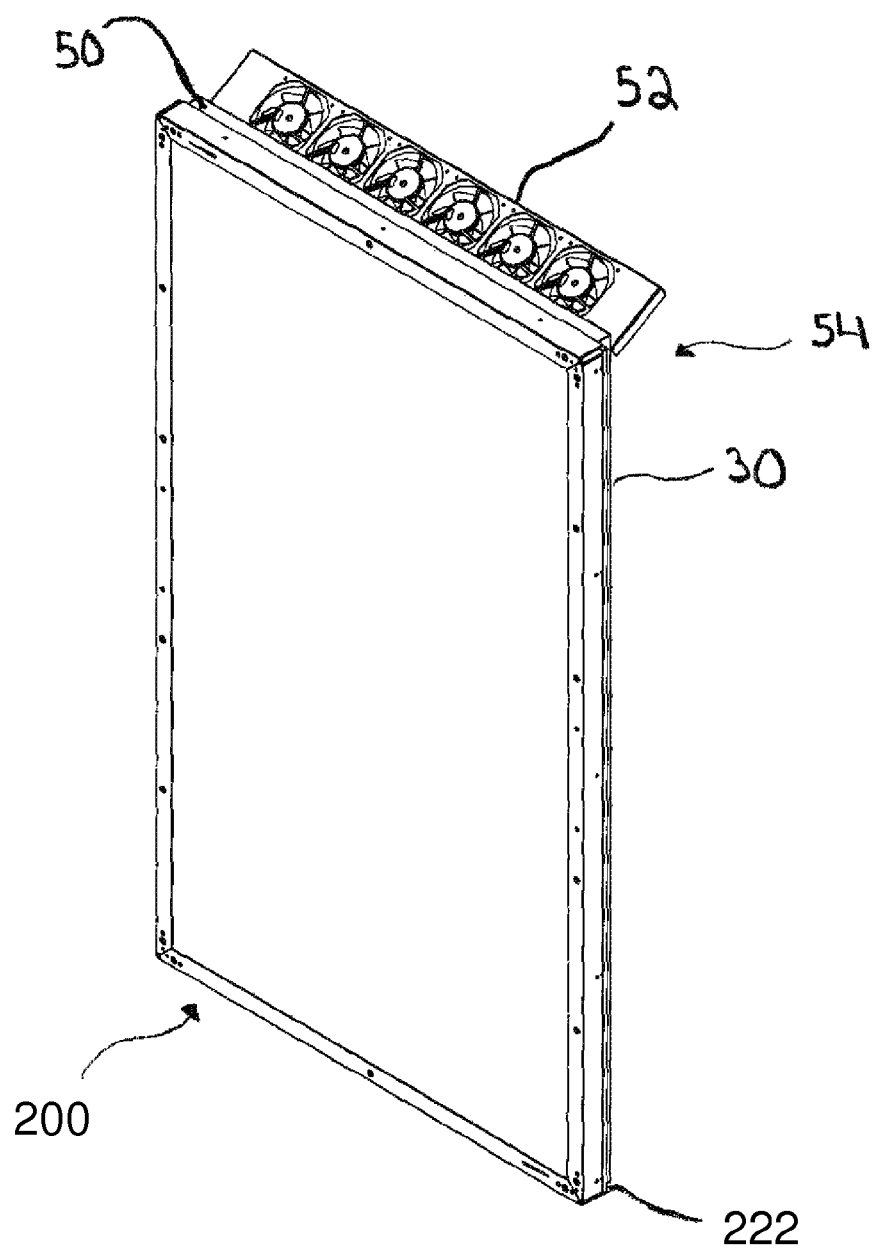
FIG. 5A is a front perspective view of a fan and display that may be used in an exemplary embodiment and an exemplary embodiment of the constricted convection plate.

As shown in FIG. 5A, an exemplary use of the PCB/LED assembly described above would be as a backlight for a liquid crystal display (LCD) 200. Here, the posterior surface 222 of the LCD 200 is the rear surface of substrate 10. In this embodiment, a constricted convection plate 30 is shown adjacent to the display posterior 222. Mounting brackets (or any other mechanical means) may be used to secure the constricted convection plate 30. The space between the constricted convection plate 30 and the display posterior 222 defines a constricted convection cooling channel 50 immediately behind the display posterior 222. In some embodiments the constricted convection cooling channel 50 may run the length and width of the LCD 200. In other embodiments, the constricted convection cooling channel 50 may be only of sufficient size to provide thermal stability to the LCD 200.

The constricted convection cooling system 54 may include a means for increasing the speed at which air travels through the constricted convection cooling channel 50. This means may include one or more fans 52 which may be positioned near an opening of the constricted convection cooling channel 50. The fans 52 may either force the air through the constricted convection channel 50 or pull the air through the constricted convection channel 50. Alternatively, a plurality of fans may be used to both push and pull air through the constricted convection cooling channel 50. The use of one or more fans 52 may provide increased velocity of the air traveling through the constricted convection cooling channel 50, thus increasing the speed with which heat is transferred from the display posterior 222.

In other exemplary embodiments, a means for cooling the air which passes through the constricted convection cooling channel 50 may be used. A means for cooling the air may include, but is not limited to, a conditioning unit, a refrigeration unit, or any other means to decrease the temperature of the air passing through the constricted convection plate 30. Alternatively, ambient air from the surroundings may be drawn in and forced within the constricted convection channel 50.

Figure 5B:
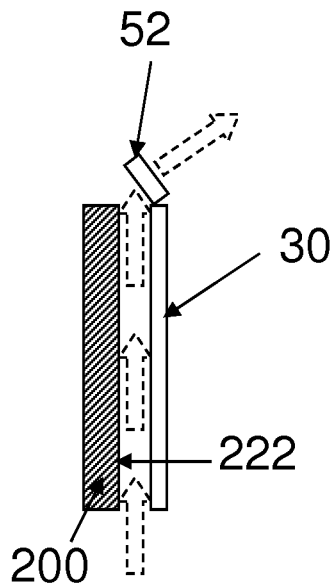
FIGS. 5B-5F show side views of additional embodiments for the constricted convection system.
Figure 5C:
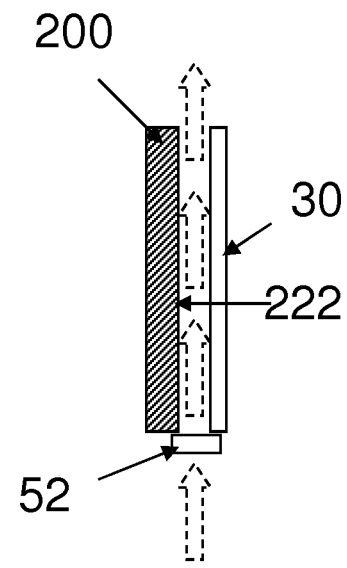
Figures 5D, 5E, 5F:
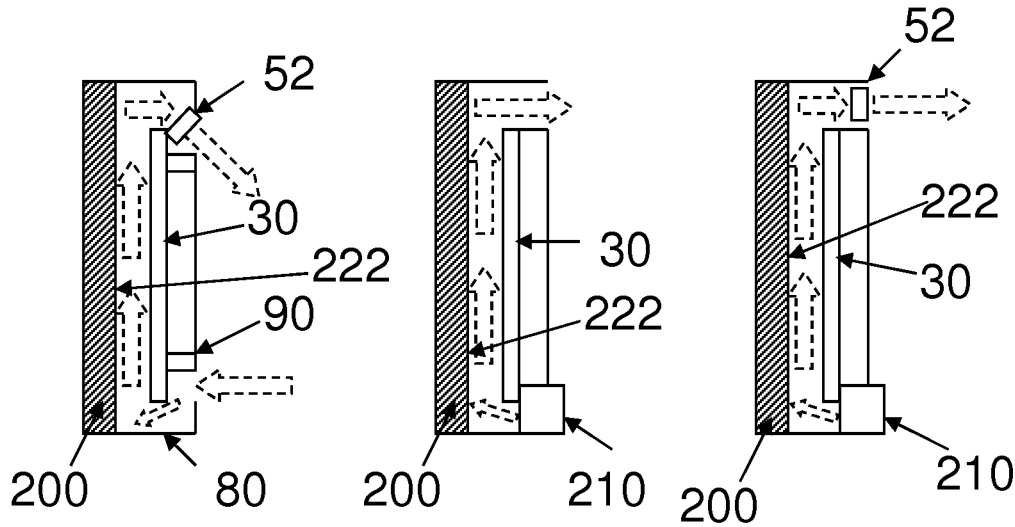

FIGS. 5B through 5F show side views of additional embodiments for the constricted convection system. In FIG. 5B, one or more fans 52 are used to draw ambient air between the posterior display surface 222 and the constricted convection plate 30. In FIG. 5C, one or more fans 52 are used to force ambient air between the posterior display surface 222 and the constricted convection plate 30. FIG. 5D is similar to FIG. 5B except that the housing 80 and the septum 90 are used to direct the flow of air. In FIG. 5E, an air conditioning unit 210 is used to both cool the air and to force the cooled air between the posterior display surface 222 and the constricted convection plate 30. Finally in FIG. 5F, an air conditioning unit 210 is used in combination with one or more fans 52.

The width of the constricted convection channel 50 may vary according to the thermal requirements of a particular application. In some embodiments, the constricted convection channel 50 may be one-half inch or less. In other embodiments, the constricted convection channel 50 may be between one-half inch and one inch. In still other embodiments, the constricted convection channel 50 may be between one and five inches.

Having shown and described preferred embodiments, those skilled in the art will realize that many variations and modifications may be made to affect the described invention and still be within the scope of the claimed invention. Additionally, many of the elements indicated above may be altered or replaced by different elements which will provide the same result and fall within the spirit of the claimed invention. It is the intention, therefore, to limit the invention only as indicated by the scope of the claims.

What is clamed is:

1. An LED illumination assembly comprising:
    a single-conducting-layer PCB having oppositely facing front and rear surfaces;
    a first group of LEDs mounted on the front surface of the PCB and connected in both parallel and series with one another by the single conduction layer;
    a second group of LEDs mounted on the front surface of the PCB and connected in both parallel and series with one another by the single conduction layer, where the second group is also connected in parallel to the first group by the single conduction layer;
    a positive conduction line on the front surface of the PCB and connecting to the first and second groups, where the positive conduction line is defined by the single conduction layer;
    a negative conduction line on the front surface of the PCB and connecting to the first and second groups, where the negative conduction line is defined by the single conduction layer;
    a constricted convection plate positioned behind the rear surface of the PCB, the space between the constricted convection plate and the rear surface of the PCB defining a cooling channel; and
    a fan positioned to force cooling air through the channel.

2. The LED illumination assembly of claim 1 wherein:
the fan is positioned to draw cooling air through the channel.

3. The LED illumination assembly of claim 1 wherein:
the PCB has an aluminum substrate.

4. The LED illumination assembly of claim 1 wherein:
the fan is positioned to push cooling air through the channel.

5. The LED illumination assembly of claim 1 wherein:
the rear surface of the PCB is metallic.

6. An LED illumination assembly comprising:
    a PCB having oppositely facing front and rear surfaces;
    a power source;
    a positive conduction line connected to the power source;
    a first group of LEDs connected in parallel with each other and connected to the positive conduction line;
    a second group of LEDs connected in parallel with each other and connected to the first group of LEDs in series;
    a third group of LEDs connected in parallel with each other and connected to the second group of LEDs in series;
    a fourth group of LEDs connected in parallel with each other and connected to the positive conduction line;
    a fifth group of LEDs connected in parallel with each other and connected to the fourth group of LEDs in series;
    a sixth group of LEDs connected in parallel with each other and connected to the firth group of LEDs in series;
    a negative conduction line connected to the third and sixth groups of LEDs and returning to the power source;
    a constricted convection plate positioned behind the rear surface of the PCB, the space between the constricted convection plate and the rear surface of the PCB defining a cooling channel; and
    a fan positioned to force cooling air through the channel.

7. The LED illumination assembly of claim 6 wherein:
the positive and negative conduction lines are defined by a single layer.

8. The LED illumination assembly of claim 6 further comprising:
    a seventh group of LEDs connected in parallel with each other and connected in series with the third group of LEDs and the negative conduction line.

9. An LED illumination assembly comprising:
    a substrate having front and rear sides;
    a layer of dielectric material placed on the front side;
    a single layer of conductive material placed atop the layer of dielectric material and electrically connecting:
        a positive conduction line,
        a first group of LEDs connected in parallel with each other and connected to the positive conduction line,
        a second group of LEDs connected in parallel with each other and connected to the first group of LEDs in series,
        a third group of LEDs connected in parallel with each other and connected to the second group of LEDs in series,
        a fourth group of LEDs connected in parallel with each other and connected to the positive conduction line,
        a fifth group of LEDs connected in parallel with each other and connected to the fourth group of LEDs in series,
        a sixth group of LEDs connected in parallel with each other and connected to the firth group of LEDs in series, and
        a negative conduction line connected to the third and sixth groups of LEDs;

a constricted convection plate positioned behind the rear side of the substrate, the space between the constricted convection plate and the rear side of the substrate defining a cooling channel; and a fan positioned to draw cooling air through the channel.

10. The LED illumination assembly of claim 9 further comprising:

a power source in electrical communication with the positive and negative conduction lines.

11. The LED illumination assembly of claim 9 wherein:
the substrate is metallic.

12. The LED illumination assembly of claim 11 wherein:
the substrate is aluminum.

13. The LED illumination assembly of claim 9 further comprising:

a second fan positioned to push cooling air through the channel.

14. The LED illumination assembly of claim 13 wherein:
the second fan is pushing cooling air that has been air conditioned.

15. A liquid crystal assembly comprising:
an LCD;
a backlight assembly placed behind the LCD, the backlight assembly having:
  a PCB having oppositely facing front and rear surfaces;
  a positive conduction line on the PCB;
  a power source electrically connected to the positive conduction line;
  a plurality of LEDs attached to the front surface of the single-layer PCB and electrically connected such that:
    a first group of LEDs connected in parallel with each other and connected to the positive conduction line,
    a second group of LEDs connected in parallel with each other and connected to the first group of LEDs in series,
    a third group of LEDs connected in parallel with each other and connected to the second group of LEDs in series,
    a fourth group of LEDs connected in parallel with each other and connected to the positive conduction line,
    a fifth group of LEDs connected in parallel with each other and connected to the fourth group of LEDs in series, and
    a sixth group of LEDs connected in parallel with each other and connected to the firth group of LEDs in series,
  a negative conduction line connected to the third and sixth group of LEDs and returning to the power source,
  a constricted convection plate positioned behind the rear surface of the PCB, the space between the constricted convection plate and the rear surface of the PCB defining a cooling channel; and
a fan positioned to force cooling air through the channel.

16. The liquid crystal assembly of claim 15 wherein:
the PCB is a metal core PCB.

17. The liquid crystal assembly of claim 15 wherein:
the PCB is aluminum.

18. The liquid crystal assembly of claim 15 wherein:
the fan is positioned to draw cooling air through the channel.

19. The liquid crystal assembly of claim 18 further comprising:
the fan is positioned to push cooling air through the channel.

* * * * *